(12) United States Patent
Bednarski et al.

(10) Patent No.: US 7,514,098 B2
(45) Date of Patent: Apr. 7, 2009

(54) USE OF TARGETED CROSS-LINKED NANOPARTICLES FOR IN VIVO GENE DELIVERY

(75) Inventors: Mark D. Bednarski, Los Altos, CA (US); Samira Guccione, Hillsborough, CA (US); King Chuen Li, Bethesda, MD (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 652 days.

(21) Appl. No.: 10/159,241

(22) Filed: May 30, 2002

(65) Prior Publication Data

US 2003/0013674 A1 Jan. 16, 2003

Related U.S. Application Data

(60) Provisional application No. 60/345,891, filed on Oct. 29, 2001, provisional application No. 60/294,309, filed on May 30, 2001.

(51) Int. Cl.
*A61K 9/127* (2006.01)
*A61K 31/70* (2006.01)
*A01N 43/04* (2006.01)
*C12N 15/00* (2006.01)
*C12N 15/88* (2006.01)

(52) U.S. Cl. .................... 424/450; 514/44; 435/455; 435/458

(58) Field of Classification Search ............... 424/450; 514/44; 435/455, 458, 320.1
See application file for complete search history.

(56) References Cited

U.S. PATENT DOCUMENTS

| | | | |
|---|---|---|---|
| 4,897,355 | A | 1/1990 | Eppstein et al. |
| 5,512,294 | A * | 4/1996 | Li et al. ................ 424/450 |
| 6,066,123 | A | 5/2000 | Li et al. |
| 6,132,764 | A * | 10/2000 | Li et al. ................ 424/450 |
| 6,187,335 | B1 * | 2/2001 | Brey et al. ............. 424/450 |
| 6,350,466 | B1 * | 2/2002 | Li et al. ................ 424/450 |
| 6,372,250 | B1 | 4/2002 | Pardridge et al. |
| 6,511,677 | B1 * | 1/2003 | Brey et al. ............. 424/450 |
| 6,852,334 | B1 * | 2/2005 | Cullis et al. ........... 424/450 |
| 2002/0022264 | A1 * | 2/2002 | Sullivan et al. ......... 435/320.1 |
| 2002/0064554 | A1 * | 5/2002 | O'Brien et al. ......... 424/450 |

OTHER PUBLICATIONS

Brannon-Peppas, Advanced Drug Delivery Reviews 56, 1649-1659, 2004.*
Shahi, Rev. Adv. Mater. Sci, vol. 5, pp. 501-509, 2003.*
Cooper et al., "Peptide MiniVectors for Gene Delivery", Angew. Chem. Int. Ed. (1999), vol. 38, No. 13/14, pp. 1949-1952.

Cooper et al., Polyamine Analogues of 3β-[N-(N',N'-Dimethylaminoethane) carbamoyl]-cholesterol (DC-Chol) as Agents for Gene Delivery**, Chem. Eur. J., (1998), vol. 4, No. 1, pp. 137-151).
Duffels et al., "Synthesis of High-Mannose Type Neoglycolipids: Active Targeting of Liposomes to Macrophages in Gene Therapy", Chem. Eur. J., (2000), vol. 6, No. 8, pp. 1416-1430.
Li et al., "Efficient Gene Delivery to Vascular Smooth Muscle Cells Using a Nontoxic, Synthetic Peptide Vector System Targeted to Membrane Integrins: A First Step Toward the Gene Therapy of Chronic Rejection[1]", (2000), vol. 70, No. 11, pp. 1616-1624.
Monnard et al., "Entrapment of nucleic acids in liposomes", Elsevier Science, (1997), vol. 1329, pp. 39-50.
Miller et al., "Cationic Liposomes for Gene Therapy**", Angew. Chem. Int. Ed., (1998), vol. 37, pp. 1768-1785.
Reimer et al., "Formation of Novel Hydrophobic Complexes between Cationic Lipids and Plasmid DNA", Biochemistry, (1995), vol. 34, pp. 12877-12883.
Sipkins et al., "Detection of tumor angiogenesis in vivo by $\alpha_v\beta_3$-targeted magnetic resonance imaging", Nature Medicine, (1998), vol. 4, No. 5, pp. 623-626.
Storrs et al., "Paramagnetic Polymerized Liposomes: Synthesis, Characterization, and Applications for Magnetic Resonance Imaging", Journal of the American Chemical Society, (1995), vol. 117, No. 28, pp. 7301-7306.
Wong et al., "Cationic Lipid Binding to DNA: Characterization of Complex Formation", Biochemistry, (1996), vol. 35, pp. 5756-5763.
Blezinger et al., "Systemic inhibition of tumor growth and tumor metastatses by intramuscular administration of the endostatin gene", Nature America, Inc., (1999), vol. 17, pp. 343-348.
Brown et al., "Gene delivery with synthetic (non viral) carriers", International Journal of Pharmaceutics, (2001), vol. 229, pp. 1-21.
Losordo et al., "Gene Therapy for Myocardial Angiogenesis Initial Clinical Results with Direct Myocardial Injection of phVEGF$_{165}$ as Sole Therapy for Myocardial Ischemia", American Heart Association, Inc., (1998), vol. 22/29, pp. 2800-.
Ruoslahti et al., "An Address System in the Vasculature of Normal Tissues and Tumors", Annu. Rev. Immunol., (2000), vol. 18, pp. 813-827.
Schnitzer, Jan, "Vascular Targeting as a Strategy for Cancer Therapy", The New England Journal of Medicine, (1998), vol. 339, pp. 472-474.

(Continued)

*Primary Examiner*—Joseph Woitach
*Assistant Examiner*—Robert M. Kelly
(74) *Attorney, Agent, or Firm*—Bozicevic, Field & Francis LLP; Pamela J. Sherwood (57) ABSTRACT

The in vivo delivery of nucleic acids is targeted by delivery of the nucleic acid in a complex with cross-linked nanoparticles; where the nanoparticles comprise cross-linked neutral amphipathic molecules, cationic amphipathic molecules and targeting amphipathic molecules. Optionally the cationic and targeting amphipathic molecules are also cross-linked. A targeting moiety present on the targeting amphipathic molecule provides for selective delivery of the complex to a predetermined target site, e.g. blood vessels, endothelial cells, tumor cells, liver cells, and the like.

14 Claims, 6 Drawing Sheets

OTHER PUBLICATIONS

Spevak et al., "Polymerized Liposomes Containing C-Glycosides of Sialic Acid: Potent Inhibitors of Influenza Virus in Vitro Infectivity", J. Am. Chem. Soc., (1993), vol. 115, pp. 1146-1147.

Storrs et al., Paramagnetic Polymerized Liposomes as New Recirculating MR Contrast Agents, JMRI, (1995), vol. 5, No. 6, pp. 719-724.

Takeshita et al., Gene Transfer of Naked DNA Encoding for Three Isoforms of Vascular Endothelial Growth Factor Stimulates Collateral Development In Vivo, Laboratory Investigation, (1996), vol. 75, No. 4, pp. 487-501.

Wang et al., "Antisense targeting of basic fibroblast growth factor and fibroblast growth factor receptor-1 in human melanomas blocks intratumoral angiogenesis and tumor growth", Nature Medicine, (1997), vol. 3, No. 8, pp. 887-893.

* cited by examiner

USE OF TARGETED CROSS-LINKED NANOPARTICLES FOR IN VIVO GENE DELIVERY

CROSS-REFERENCE TO RELATED APPLICATIONS

This Application claims benefit of priority to U.S. Provisional patent application 60/345,891, filed Oct. 29, 2001; and claims benefit of priority of U.S. Provisional patent application 60/294,309, filed May 30, 2001.

BACKGROUND OF THE INVENTION

Gene therapy is a powerful technology for treatment of a variety of diseases. The earliest applications of gene therapy were based on the principle that when a disease is caused by a faulty gene or combination of genes, the disease might be controlled, prevented or cured by replacement of the faulty gene with a functional version. Gene therapy has been applied to many different genetic diseases in this context, including ADA deficiency, familial hypercholesterolaemia and cystic fibrosis. Several clinical trials employing gene therapy protocols have already been completed with some success in patients, although the effectiveness of the protocols can be limited by the inefficiency of the gene transfer vectors. Gene therapy has also been applied to a variety of protocols that involve an element of gene transfer, but which do not involve correction of a genetic defect.

Methods for the transfer of foreign genes into eukaryotic cells are essential to the development of gene therapy strategies. To this end, different mammalian expression vector systems have been designed. The choice of a particular expression system depends on the nature and purpose of the study and involve selecting particular parameters of expression systems such as the type of promoter/enhancer sequences, the type of expression (transient versus stable) and the level of desired expression. In addition to the vector itself, the formulation of the nucleic acid for in vivo delivery must be considered. Numerous approaches have been developed to facilitate the transfer of genes into cells via physical, chemical or viral strategies. While these systems have all been effective in vitro they do not necessarily lead to effective in vivo transfection.

Although liposome DNA delivery systems have been assessed in gene therapy clinical trials, there are concerns about inefficiency of liposome-based gene transfer technology. While many approaches have been taken to improve transfection efficiency, because of the complex nature of the formulation technology it is difficult to define specific carrier attributes that enhance transfection.

Methods of gene delivery in vivo that provide for efficient and targeted delivery of the desired sequence are of great interest for clinical and scientific uses. The present invention addresses this issue.

RELEVANT LITERATURE

Miller (1998) Angew. Chem. Int. Ed. 37:1768-1785; and Brown et al. (2001) Int J Pharm 229(1-2):1-21 review gene therapy methods utilizing non viral carriers, including cationic lipids.

Polymerized vesicles are discussed in Spevak et al. (1993) J. Am. Chem. Soc. 115:1146-1147; Storrs et al. (1995) J. Am. Chem. Soc. 117:7301-7306; and Storrs et al. (1995) J. Magn. Reson. Imaging. 5:719-724. U.S. Pat. No. 6,132,764, Li et al. discloses targeted polymerized liposome diagnostic and treatment agents.

Targeted gene delivery to the vasculature is discussed in Blezinger et al. (1999) Nat Biotechnology 17:343-348; Wang and Becker (1997) Nature Medicine 3:887-893; Takeshita et al. (1996) Lab Invest 75:487-501; Losordo et al. (1998) Circulation 98:2800-2804; Schnitzer (1998) New Eng. J. Med. 339(7):472-474; and Ruoslahti (2000) Ann. Rev. Immunol. 18:813-827.

Magnetic resonance imaging (MRI) using a paramagnetic contrast agent targeted to endothelial alphaVbeta3 via a monoclonal antibody is disclosed by Sipkins et al. (1998) Nat. Medicine 4:623-626.

SUMMARY OF THE INVENTION

Methods are provided for in vivo delivery of nucleic acids to a target tissue, utilizing nucleic acids complexed with cross-linked nanoparticles comprising a targeting moiety. The cross-linked nanoparticles preferably comprise, in part, cationic amphipathic molecules.

BRIEF DESCRIPTION OF THE DRAWINGS

FIG. 1. Passage 4 human umbilical vein endothelial cells (Clontech, Palo Alto, Calif.) grown on 35 mm collagen-coated dishes were cultured in F-10 media containing 1% FBS. The luciferase vector (0.5 μgs of the pGL2 luciferase vector from Promega, Madison, Wis.) was electrostatically coupled to 15 nanomoles of the NPs and incubated with the endothelial cells in culture for 6 hours. Media was then replaced with MCDB-131 containing 20% fetal bovine serum for 20 hours. Cells were then lysed with reporter lysis buffer (Promega, Madison, Wis.) and luciferase expression measured using the Promega luciferase assay system according to manufacturer's directions. Luciferase activity is reported as luciferase protein content, as determined using a standard curve of recombinant luciferase enzyme, normalized to total cellular protein content as determined by the Bradford reagent protein assay method (Sigma, St. Louis, Mo.). The numerical values for the luciferase expression are as follows: (1) Anionic targeted NP1-plasmid complex 0.0034+/−0.0081 pg luciferase/μg protein; (2) Cationic untargeted NP2-plasmid complex 0.0038+/−0.00079 pg luciferase/μg protein; (3) Cationic targeted NP3-plasmid complex 0.078+/−0.015 pg luciferase/μg protein. The fold increase was calculated by dividing (3) and (2).

FIG. 2. Scheme outlining the formation of the nanoparticles (NPs) by self-assembly and polymerization of the appropriate lipids. The trivalent lipid-integrin antagonist 1 was combined with diacetylene phospholipid 2 in a chloroform solution, to which the cationic lipid 3 was added to vary the surface charge. The surface density of the integrin antagonist on the NPs was set at 10 mole % of the concentration of compound 2. The mean diameter of the NPs were between 40 nm and 50 nm as determined by dynamic light scattering and the zeta potential was approximately +35 for the NPs used in this study. The NPs were stable for months without significant changes in their physical and biological properties when formulated for use in vivo.

FIGS. 3A and 3B. $\alpha v\beta 3$-NP-mediated gene delivery to $\alpha v\beta 3$ bearing cells in vitro and in vivo. (A) GFP gene transfer mediated by $\alpha v\beta 3$-NP to M21 or M21-L human melanoma cells was evaluated. (B) Athymic WEHI mice were subcutaneously injected with M21-L cells ($5\times 10^6$) and tumors were allowed to grow to ~100 mm$^3$. Mice were then injected i.v. with 450 nanomoles of NP electrostatically coupled to 25 μgs of plasmid expressing firefly luciferase, while one group received a co-injection of 20-fold molar excess of the soluble αvβ3-targeting ligand. After 24 hours, mice were sacrificed, tissues surgically removed, and luciferase activity quantified. Inset shows luciferase expression as a function of DNA dose injected. Each bar represents the mean +/−SD of five replicates.

FIGS. 4A-4C. Delivery of ATP$^\square$-Raf to tumor-associated blood vessels causes endothelial and tumor cell apoptosis. (A-C) Athymic WEHI mice were subcutaneously implanted with M21-L melanoma, and tumors were allowed to grow to ~400 mm$^3$. Mice were then given a single i.v. injection of αvβ3-NP-Raf(−). Control animals were injected with the αvβ3-NP coupled to a shuttle vector. After 24 or 72 hours mice were sacrificed, their tumors resected, fixed, sectioned and stained. (A) Tumors harvested 24 hours after treatment were immunostained for VE-Cadherin (endothelial cells), FLAG (gene expression), and TUNEL (apoptosis) (bar=50 μM). Asterisks denote blood vessels. (B) Tumors harvested 72 hours after treatment were stained as above (bar=50 μM). Arrowheads denote ring of tumor cells undergoing apoptosis. (C) Tumors harvested 72 hours after treatment with αvβ3-NP-Raf(−) (left and center panel) or controls (right panel) were stained with hematoxylin and eosin. Necrotic tissues are denoted by N (bar=50 μM, left panel and 100 μM, center and right panel).

FIGS. 5A-5D. Delivery of mutant Raf to tumor vessels inhibits angiogenesis causing regression of established tumors. (A) Athymic WEHI mice implanted subcutaneously with M21-L melanoma cells were allowed to form ~400 mm$^3$ tumors followed by i.v. injection with αvβ3-NP-Raf(−) as in FIG. 4. Tx=start of treatment, S=sacrifice of animals due to large tumor burden. ◆=PBS control, ■=αvβ3-NP-shuttle vector, ●=αvβ3-NP-Raf(−), σ=αvβ3-NP-Raf (−)+excess soluble αvβ3 ligand. Each point represents the mean+/−SE of six replicates. (inset) Tumors from the PBS control and from the αvβ3-NP-Raf(−) group were sectioned, stained with an antibody directed against VE-Cadherin to enumerate blood vessels per 200× microscopic field. Each bar represents the mean+/−SD of 5 replicates. (B-D) Pulmonary or hepatic metastases of CT-26 colon carcinoma cells were formed in Balb/C mice by i.v. or splenic injection, respectively. Metastatic tumors were allowed to grow for 10 days before mice were injected i.v. on days 10 and 17. Organs were harvested on day 24 (B and C) or at indicated time-points (D), weighed (B-D) and photographed. (D) Each bar represents the mean of +/−SD of 6-8 mice. (*, p<0.05).

DESCRIPTION OF THE PREFERRED EMBODIMENTS

The in vivo delivery of nucleic acids is enhanced by delivery of the nucleic acid in a complex with nanoparticles; where the nanoparticles comprise cross-linked neutral amphipathic molecules, cationic amphipathic molecules and targeting amphipathic molecules. Optionally the cationic and targeting amphipathic molecules are also cross-linked. A targeting moiety present on the targeting amphipathic molecule provides for selective delivery of the complex to a predetermined target site, e.g. blood vessels, tumor cells, liver cells, and the like.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a microsphere" includes a plurality of such microspheres and reference to "the stent" includes reference to one or more stents and equivalents thereof known to those skilled in the art, and so forth.

Cross-linked nanoparticles. As used in the methods of the invention, cross-linked nanoparticles, or NP, are self-assembled aggregates of amphipathic molecules, where the nanoparticle is stabilized by cross-linking. The amphipathic molecules include cationic molecules, neutral molecules, and targeting molecules, where the targeting molecule comprises a targeting moiety, usually a targeting moiety attached to a head group.

Suitable amphipathic molecules have a structure as shown below, comprising a hydrophilic head group, which may be a chemically reactive head group; a linker or covalent bond between the head and tail groups; and a hydrophobic tail group for self-assembly into nanoparticles. The molecules comprise a cross-linking group to stabilize the nanoparticle, which cross-linking group may comprise all or part of the tail group and/or the linker. A mixture of molecules may provide different functional groups on the hydrophilic exposed surface. For example, some hydrophilic head groups may have functional surface groups, for example, biotin, amines, cyano, carboxylic acids, isothiocyanates, thiols, disulfides, α-halocarbonyl compounds, α,β-unsaturated carbonyl compounds and alkyl hydrazines for attachment of targeting moieties.

Amphiphilic molecules suitable for constructing targeting nanoparticles have a hydrophilic head group and a hydrophobic tail group, where the hydrophobic group and hydrophilic group are joined by a covalent bond, or by a variable length linker group. The linker portion may be a bifunctional aliphatic compounds which can include heteroatoms or bifunctional aromatic compounds. Preferred linker portions include, e.g. variable length polyethylene glycol, polypropylene glycol, polyglycine, bifunctional aliphatic compounds, for example amino caproic acid, or bifunctional aromatic compounds.

Amphipathic molecules of interest include lipids, which group includes fatty acids, neutral fats such as triacylglycerols, fatty acid esters and soaps, long chain (fatty) alcohols and waxes, sphingoids and other long chain bases, glycolipids, sphingolipids, carotenes, polyprenols, sterols, and the like, as well as terpenes and isoprenoids. For example, molecules such as diacetylene phospholipids may find use as neutral amphipathic molecules.

At least a portion of the amphipathic molecules in the NP are cationic amphipathic molecules. Nucleic acids are polyanionic molecules which bind cations and other positively-charged carriers through charge interactions. Cationic amphipathic molecules form tight complexes with the nucleic acid, thereby condensing it and protecting it from nuclease degradation. In addition, polycationic nanoparticles may act to mediate transfection by improving association with negatively-charged cellular membranes by giving the complexes a positive charge; masking the nucleic acid from neutralizing antibodies or opsonins which are in circulation; increasing systemic circulation time by reduction of non-specific clearance mechanisms in the body, i.e. macrophages, etc.; decreasing immunogenicity; and/or enhancing transport from the cytoplasm to the nucleus where DNA may be transcribed.

The size of the nanoparticles can be controlled, e.g. by extrusion, sonication, etc. Preferably the nanoparticles are at least about 10 nm in diameter and not more than about 250 nm in diameter, more usually at least about 35 nm in diameter and not more than about 100 nm in diameter, and may be from about 40 nm in diameter to from about 50 nm in diameter. The zeta potential for nanoparticles comprising cationic amphipathic molecules may range from at least about +5 mV to not more than about +75 mV, more usually from at least about +20 mV to not more than about +50 mV. The nanoparticle may be a single layer (micelle) bilayer (unilamellar) or more than one bilayer (multilamellar), and is usually a lipid bilayer.

The component amphipathic molecules of the targeting nanoparticles of this invention may be purified and characterized individually using standard, known techniques and then combined in controlled fashion to produce the final particle. The nanoparticles may be constructed to mimic native cell membranes or present functionality, such as ethylene glycol derivatives, that can reduce their potential immunogenicity. Additionally, the cross-linked nanoparticles of this invention have a well defined structure that can be characterized by known physical techniques such as transmission electron microscopy and atomic force microscopy.

The targeting nanoparticles are mixed with nucleic acids, and complexes form by charge interactions between the cationic components and the negative charges of the nucleic acids. The nucleic acid may be in any physical form, e.g., linear, circular or supercoiled; single-stranded, double-, triple-, or quadruple-stranded; and further including those having naturally occurring nitrogenous bases and phosphodiester linkages as well as non-naturally occurring bases and linkages, e.g. for stabilization purposes. Preferably it is in the form of supercoiled plasmid DNA. Plasmid DNA is conveniently used for DNA transfections since there are no size constraints on the DNA sequences that may be included, and it can be produced in large quantity by growing and purifying it from bacterial cells.

Cross-linking amphipathic molecules. The neutral amphipathic molecules, and optionally the targeting and cationic amphipathic molecules, comprise a crosslinking functional group, e.g. diacetylene, olefins, acetylenes, nitrites, alkyl styrenes, esters, thiols, amides, αβunsaturated carbonyl compounds, etc. in the linker or tail group of the molecule. The cross-linking groups irreversibly cross-link, or polymerize, when exposed to ultraviolet light or other radical, anionic or cationic, initiating species, while maintaining the distribution of functional groups at the surface of the nanoparticle. The resulting cross-linked nanoparticle is stabilized against fusion with cell membranes or other liposomes and stabilized towards enzymatic degradation. The cross-linking functional groups may be located at specific positions on hydrophobic portion of the amphipathic molecule.

After initiation of cross-linking, oligomers of at least two and not more than about 100 monomeric amphipathic molecules are formed, usually at least two and not more than about 30 monomers are present in the cross-linked oligomer.

Cationic amphipathic molecules. Cationic amphipathic groups include any amphiphilic molecule as described above, including lipids, synthetic lipids and lipid analogs, having hydrophobic and hydrophilic moieties, a net positive charge, and which by itself can form spontaneously into bilayer vesicles or micelles in water. The term also includes any amphipathic molecules that can be stably incorporated into lipid micelle or bilayers in combination with phospholipids, with its hydrophobic moiety in contact with the interior, hydrophobic region of the micelle or bilayer membrane, and its polar head group moiety oriented toward the exterior, polar surface of the membrane.

The term "cationic amphipathic molecules" is intended to encompass molecules that are positively charged at physiological pH, and more particularly, constitutively positively charged molecules, comprising, for example, a quaternary ammonium salt moiety. Cationic amphipathic molecules used for gene delivery typically consist of a hydrophilic polar head group and lipophilic aliphatic chains. Similarly, cholesterol derivatives having a cationic polar head group may also be useful. See, for example, Farhood et al. (1992) *Biochim. Biophys. Acta* 1111:239-246; Vigneron et al. (1996) *Proc. Natl. Acad. Sci.* (USA) 93:9682-9686.

Cationic amphipathic molecules of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include DOTIM (also called BODAI) (Solodin et al., (1995) Biochem. 34: 13537-13544), DDAB (Rose et al., (1991) BioTechniques 10(4):520-525), DOTMA (U.S. Pat. No. 5,550,289), DOTAP (Eibl and Wooley (1979) Biophys. Chem. 10:261-271), DMRIE (Felgner et al., (1994) J. Biol. Chem. 269(4): 2550-2561), EDMPC (commercially available from Avanti Polar Lipids, Alabaster, Ala.), DCChol (Gau and Huang (1991) Biochem. Biophys. Res. Comm. 179:280-285), DOGS (Behr et al., (1989) Proc. Natl. Acad. Sci. USA, 86:6982-6986), MBOP (also called MeBOP) (WO 95/14651), and those described in WO 97/00241. In addition, nanoparticles having more than one cationic species may be used to produce complexes according to the method of the present invention.

Targeting amphipathic molecule. A targeting amphipathic molecule has the structure as described above, comprising a hydrophilic and a hydrophobic group, and further comprises a targeting moiety, usually a targeting moiety covalently or non-covalently bound to the hydrophilic head group. Head groups useful to bind to targeting moieties include, for example, biotin, amines, cyano, carboxylic acids, isothiocyanates, thiols, disulfides, α-halocarbonyl compounds, α,β-unsaturated carbonyl compounds, alkyl hydrazines, etc. The amphipathic molecule provides a component of the cross-linked nanoparticle, and the bound targeting moiety resides on the exterior of the nanoparticle, where it is accessible for interaction. Preferably the targeting moiety is bound to the amphipathic molecule prior to synthesis of the nanoparticle, however in some cases the targeting moiety will be added to preformed nanoparticles.

Chemical groups that find use in linking a targeting moiety to an amphipathic molecule also include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hyrodrazone, lipids, and the like, as known in the art.

The linkage between targeting moiety and amphipathic molecules may comprise spacers, e.g. alkyl spacers, which may be linear or branched, usually linear, and may include one or more unsaturated bonds; usually having from one to about 300 carbon atoms; more usually from about one to 25 carbon atoms; and may be from about three to 12 carbon atoms. Spacers of this type may also comprise heteroatoms or functional groups, including amines, ethers, phosphodiesters, and the like. Specific structures of interest include: $(CH_2CH_2O)_n$ where n is from 1 to about 12; $(CH_2CH_2NH)_n$, where n is from 1 to about 12; $[(CH_2)_n(C=O)NH(CH_2)_m]_z$, where n and m are from 1 to about 6, and z is from 1 to about 10; $[(CH_2)_nOPO_3(CH_2)_m]_z$ where n and m are from 1 to about 6, and z is from 1 to about 10. Such linkers may include polyethylene glycol, which may be linear or branched.

The targeting moiety may be joined to the amphipathic molecule through a homo- or heterobifunctional linker having a group at one end capable of forming a stable linkage to the hydrophilic head group, and a group at the opposite end capable of forming a stable linkage to the targeting moiety. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP); N, N'-(1,3-phenylene) bismaleimide; N, N'-ethylene-bis-(iodoacetamide); or 4-(N-maleimidomethyl)-cyclohexane-1-carboxylic acid N-hydroxysuccinimide ester (SMCC); m-maleimidobenzoyl-N-hydroxysuccinimide ester (MBS), and succinimide 4-(p-maleimidophenyl)butyrate (SMPB), an extended chain analog of MBS. The succinimidyl group of these cross-linkers reacts with a primary amine, and the thiol-reactive maleimide forms a covalent bond with the thiol of a cysteine residue.

Other reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1, 4-disulfonylchloride (which reacts principally with amino groups); hexamethylenediisocyanate or diisothiocyanate, or azophenyl-p-diisocyanate (which reacts principally with amino groups); disdiazobenzidine (which reacts primarily with tyrosine and histidine); O-benzotriazolyloxy tetramethuluronium hexafluorophosphate (HATU), dicyclohexyl carbodiimde, bromo-tris (pyrrolidino) phosphonium bromide (PyBroP); N,N-dimethylamino pyridine (DMAP); 4-pyrrolidino pyridine; N-hydroxy benzotriazole; and the like. Homobifunctional cross-linking reagents include bis-maleimidohexane ("BMH").

For example, targeting molecules may be formed by converting a commercially available lipid, such as DAGPE, a PEG-PDA amine, DOTAP, etc. into an isocyanate, followed by treatment with triethylene glycol diamine spacer to produce the amine terminated thiocarbamate lipid which by treatment with the para-isothiocyanophenyl glycoside of the targeting moiety produces the desired targeting glycolipids. This synthesis provides a water soluble flexible linker molecule spaced between the amphipathic molecule that is integrated into the nanoparticle, and the ligand that binds to cell surface receptors, allowing the ligand to be readily accessible to the protein receptors on the cell surfaces.

Targeting moiety. A targeting moiety, as used herein, refers to all molecules capable of specifically binding to a particular target molecule and forming a bound complex as described above. Thus the ligand and its corresponding target molecule form a specific binding pair.

The term "specific binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

Examples of targeting moieties include, but are not limited to antibodies, lymphokines, cytokines, receptor proteins such as CD4 and CD8, solubilized receptor proteins such as soluble CD4, hormones, growth factors, peptidomimetics, synthetic ligands, and the like which specifically bind desired target cells, and nucleic acids which bind corresponding nucleic acids through base pair complementarity. Targeting moieties of particular interest include peptidomimetics, peptides, antibodies and antibody fragments (e.g. the Fab' fragment). For example, β-D-lactose has been attached on the surface to target the aloglysoprotein (ASG) found in liver cells which are in contact with the circulating blood pool.

Cellular targets include tissue specific cell surface molecules, for targeting to specific sites of interest, e.g. neural cells, liver cells, bone marrow cells, kidney cells, pancreatic cells, muscle cells, and the like. For example, nanoparticles targeted to hematopoietic stem cells may comprise targeting moieties specific for CD34, ligands for c-kit, etc. Nanoparticles targeted to lymphocytic cells may comprise targeting moieties specific for a variety of well known and characterized markers, e.g. B220, Thy-1, and the like.

Endothelial cells are a target of particular interest, in particular endothelial cells found in blood vessels, e.g. during angiogenesis, inflammatory processes, and the like. Among the markers present on endothelial cells are integrins, of which a number of different subtypes have been characterized. Integrins can be specific for endothelial cells involved in particular physiological processes, for example certain integrins are associated with inflammation and leukocyte trafficking (see Alon & Feigelson (2002) *Semin Immunol.* 14(2): 93-104; and Johnston & Butcher (2002) *Semin Immunol* 14(2):83-92, herein incorporated by reference). Targeting moieties specific for molecules such as ICAM-1, VCAM-1, etc. may be used to target vessels in inflamed tissues.

Endothelial cells involved in angiogenesis may be targeted for site directed delivery of nucleic acids. Diseases with a strong angiogenesis component include tumors growth, particularly solid tumor growth, psoriasis, macular degeneration, rheumatoid arthritis, osteoporosis, and the like. A marker of particular interest for angiogenic endothelial cells is the $\alpha v \beta 3$ integrin. Ligands for this integrin are described, for example, in U.S. Pat. Nos. 5,561,148; 5,776,973; and 6,204,280; and in International patent publications WO 00/63178; WO 01/10841; WO 01/14337; and WO 97/45137, herein incorporated by reference.

Synthesis of targeting nanoparticles. To synthesize targeting nanoparticles, the component amphipathic molecules are mixed in an aqueous environment. The percentage of cationic amphipathic molecules is selected to provide for the desired zeta potential, and is usually at least about 5% of the total amphipathic molecules by weight, and not more than about 40%, usually at least about 10% and not more than about 30%. The percentage of targeting amphipathic molecules is usually at least about 1% of the total amphipathic molecules by weight and not more than about 20%, usually at least about 5% and not more than about 15%. The balance of the amphipathic molecules are comprised of neutral, crosslinking molecules.

The components are mixed, usually with the application of energy, e.g. heat, and are allowed to self-assemble. Following assembly, cross-linking is induced by a suitable method, e.g. addition of radical initiator, redox agents, light, etc., to be determined by the nature of the cross-linking group. The targeting properties of the nanoparticle may be tested in a binding assay, conveniently performed in vitro. One such assay is described in the Examples, but those of skill in the art will appreciate that a variety of assays may be used for this purpose.

Formulation of nucleic acids complexed with targeting nanoparticles. After formation of the nanoparticles, the nanoparticles are complexed with nucleic acid. Such complex formation is generally performed in the substantial absence of salts, e.g. K+, Ca++, Mg++, Na+, and the like. Preferably the complex is formed in a neutral media, e.g. comprising saccharides, such as sucrose, dextrose, glycols, and the like, at a concentration of from about 1% to about 20%, usually from about 5% to about 15%. The nucleic acid is mixed slowly with the nanoparticles, at a rate sufficiently slow that the complexes that are formed are less than about 400 nm in diameter. The resulting complexes, which are suitable for in vivo administration, will generally range from about 100 nm to about 250 nm in size, and will have a generally neutral zeta potential, from about −10 to about +10 mV. The complexes are highly stable, and can be stored for long periods of time without loss of activity.

For in vivo administration, the complexes may be administered in a physiologically acceptable low salt medium, for example the neutral media described above, or may be dialyzed or diluted into a low salt buffer, e.g. comprising MOPS, HEPES, histidine, etc. The medium for administration may also comprise carrier protein, e.g. albumin, and the like.

METHODS OF USE

The methods of the invention may be practiced with any mammalian species, including canines; felines; equines; bovines; ovines; etc. and primates, particularly humans. Animal models, particularly small mammals, e.g. murine, lagomorpha, etc. are of interest for experimental investigations. The methods of the invention provide a platform for delivery of genetic materials and thus is useful in a variety of applications. Nucleic acids that correct genetic deficiencies can be introduced into a targeted tissue, including blood vessels, solid tissues, e.g. pancreatic cells for the treatment of diabetes, liver cells to treat hepatic deficiencies, etc.

Also of interest is the delivery of nucleic acids to accomplish genetic immunization. Genetic immunization involves delivery of a nucleic acid to cells for expression of the encoded immunogen within the target tissue. A preferred target tissue is muscle cells. An immune response against the immunogen is mounted in the animal, resulting in development of humoral and/or cellular immunity. Administration of nucleic acids according to the method of the invention, which results in genetic alteration of muscle cells and induction of an immune response can be used to elicit protective immunity.

The method of the invention is also useful in a variety of other settings in which genetic alteration of tissue is desirable. For example, the method of the invention can be used to introduce exogenous coding sequences into solid tumors, where the encoded gene product provides for recruitment of immune cells, induces apoptosis, inhibits angiogenesis, etc. in the tumor. Transgenic animals are created by transfection of targeted tissues with a nucleic acid of interest.

The nucleic acid materials for delivery to targeted tissue will usually comprise a nucleic acid of interest that encodes a gene product for which expression is desired, and a promoter for expression of the gene product. By "nucleic acid of interest" is meant any DNA, RNA or analog thereof that encodes a polypeptide or other gene product that is desirable for expression in tissue of a subject. The gene product can include a polypeptide, an anti-sense mRNA, or other gene product that is desirably expressed. The term "DNA of interest" or "DNA" is used herein as shorthand to refer to the nucleic acid of interest and is not meant to be limiting. The nucleic acid delivered to the tissue in vivo can take any number of forms. For example, the nucleic acid can be introduced as a linear or circular molecule, preferably a circular molecule (e.g., a circular plasmid or other construct).

The nucleic acid of interest and a promoter may be operably linked to provide a construct, or vector for expression. Normally, "construct" will refer to a nucleic acid molecule that facilitates expression of a gene product encoded by the nucleic acid to be introduced. By "operably linked" is meant that a DNA sequence and a regulatory sequence(s) (e.g., a promoter sequence) are connected in such a way as to permit transcription when the appropriate molecules (e.g., transcriptional activator proteins) are bound to the regulatory sequence(s).

It will be recognized by those skilled in the art that the optimal quantity and spacing of individual dosages of nucleic acids will be determined by the precise form and components of the nucleic acid formulation to be delivered, the site of administration, the use to which the method is applied (e.g., immunization, treatment of a condition, production of transgenic animals, etc.), and the particular subject to which the nucleic acid formulation is to be delivered, and that such optimums can be determined by conventional techniques. It will also be appreciated by one skilled in the art that the optimal dosing regimen, i.e., the number of doses of nucleic acids, can be ascertained using conventional methods, e.g., course of treatment determination tests. Generally, a dosing regimen will involve administration of the selected nucleic acid formulation at least once, and may be performed multiple times over a period of days or weeks.

The amount of DNA/nanoparticle complex required to accomplish expression of a desired gene product at an effective level (e.g. a level effective to elicit an immune response, to alleviate a symptom of a condition or disease, etc.) will vary according to the desired effect (e.g. immunity, prophylaxis, tumor diminution, etc.), as well as with other variables such as the age of the subject, the tissue to be genetically altered, the gene product to be expressed and the desired level of its expression, etc. In general, the amount of DNA/nanoparticle complex administered is an amount sufficient to provide for transformation of a number of cells that in turn provides for a level of gene product expression from the introduced DNA/nanoparticle complex to provide for a desired effect. Dosages are routinely determined in the art, and can be extrapolated from the amounts of DNA/nanoparticle complex effective in an animal mode (e.g., a rodent (mouse or rat) or other mammalian animal model), in which factors such as the efficiency of transformation and the levels of gene product expression achieved can be readily assessed and extrapolated to other vertebrate subjects. Generally speaking, the amount of DNA that is delivered to a human is usually on the order of about 100 times the amount of DNA effective in a rat.

The present invention is not limited to any particular nucleic acid coding for any particular polypeptide or other gene product, and the nucleic acid selected will vary with the aim the method is intended to accomplish, e.g. genetic immunization, delivery of a polypeptide for replacement or enhancement therapy, production of transgenic animals as models of a condition or disease, delivery of a gene for gene replacement therapy, delivery of a gene that induces cell death, apoptosis, arrest of proliferation, etc. Exemplary gene products that can be expressed in genetically modified cells according to the invention are discussed in more detail below. Plasmids containing genes coding for a large number of physiologically active polypeptides and other gene products, as well as for antigens or immunogens, have been reported in the literature and can be readily obtained by those of skill in the art.

In a preferred embodiment, the nucleic acids of the invention encode a biologically active polypeptide, such as an immunity-conferring polypeptide, e.g. for genetic immunization, or a therapeutic polypeptide, e.g. for amelioration of a symptom associated with a polypeptide deficiency, or for reduction of a tumor, or tumor vasculature, e.g. by inducing cell death. A polypeptide is understood to be any translation product of a nucleic acid regardless of size and glycosylation. The gene product can be any gene product that exhibits a desired biological activity, e.g. a functional characteristic such as enzymatic activity, or DNA binding; or structural characteristic such as role in cell architecture or presentation of one or more immunity-conferring epitopes in the host cell cytoplasm, nucleus, or membrane. Alternatively or in addition, the gene product may exhibit a desired biological activity following expression and secretion from the transformed cell.

Immunity-conferring polypeptides include those polypeptides that comprise an epitope that upon exposure to the immune system of a vertebrate (generally, a mammal), either alone or in the presence of a molecule that facilitates immune response induction (known in the immunology art as a carrier molecule), can act as an endogenous immunogen to provoke a humoral immune response, a cellular immune response, or both.

Any nucleic acid construct having a eukaryotic promoter operably linked to a DNA of interest can be used in the invention. For example, a bacterial plasmid, viral construct, or other DNA construct can be genetically engineered to provide a recombinant DNA molecule having a sequence encoding the desired gene product. Preferably the construct is capable of replication in both eukaryotic and prokaryotic hosts, which constructs are known in the art and are commercially available. The nucleic acid, or nucleic acid-containing construct, can be purified according to methods well known in the art and provided in a delivery formulation as described below.

The nucleic acid of interest can be obtained from any of a variety of sources or methods well known in the art, e.g. isolated from suitable cells, produced using synthetic techniques, etc., and the constructs prepared using recombinant techniques well known in the art. Likewise, techniques for obtaining expression of DNA or RNA sequences in a genetically altered host cell are known in the art (see, for example, Kormal et al., *Proc. Natl. Acad. Sci. USA,* 84:2150-2154, 1987; Sambrook et al. *Molecular Cloning: A Laboratory Manual,* 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Preferably, the DNA construct contains a promoter to facilitate expression of the DNA of interest. The promoter used will vary with the intended aim of the method of the invention. For example, where the method is to be used to accomplish genetic immunization or treatment of tumors, the promoter may be a strong, constitutive eukaryotic promoter such as a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., *Cell* 41:521-530, 1985) and the promoter from the long terminal repeat (LTR) of RSV (Gorman et al., *Proc. Natl. Acad. Sci. USA* 79:6777-6781, 1982).

Sequences of many of the gene products desirable for delivery according to the method of the invention are known. The sequences have been described in the literature, are available in public sequence databases such as GenBank, or are otherwise publicly available. With the availability of automated nucleic acid synthesis equipment, both DNA and RNA can be synthesized directly when the nucleotide sequence is known, or synthesized by PCR cloning followed by growth in a suitable microbial host. Moreover, when the amino acid sequence of a desired polypeptide is known, a suitable coding sequence for the nucleic acid can be inferred. Where the DNA encoding a gene product of interest has not been isolated, this can be accomplished by various, standard protocols well known to those of skill in the art (see, for example, Sambrook et al., ibid; Suggs et al. 1981 *Proc. Natl. Acad. Sci. USA* 78:6613-6617; U.S. Pat. No. 4,394,443; each of which are incorporated herein by reference with respect to identification and isolation of DNA encoding a gene product of interest).

Expression of the introduced nucleic acid can be short-term, i.e. a few hours to several hours to a few days, or permanent or long-term i.e. from a week to several weeks to a few months or more. In general, gene product expression from the introduced nucleic acid ranges from at least about 1 to 2 days, or 3 to 5 days, to about 1 week, generally about 1 to 4 weeks, up to about 6 weeks, and may be as long as about 10 to 12 weeks or longer. The short-term nature of gene product expression can be due to loss of the introduced nucleic acid, inactivation of the nucleic acid, and/or natural maturation and sloughing off of the transformed cell. Where expression times of more than a few weeks are desired, for example from about 10 to 12 weeks or longer, expression of the gene product can be maintained by using a retroviral construct having inactivated LTRs and an internal promoter in the construct to drive gene product expression.

Various conditions, diseases, and/or symptoms thereof are amenable to treatment via the biological effect of a gene product delivered to the subject using the methods of the invention. The specific gene product delivered using the method of the invention will, of course, vary with the condition, disease, or symptom from which the subject desires relief. Exemplary conditions and diseases, as well as their attendant symptoms, that are amenable to treatment by expression of an appropriate gene product in the targeted tissue(e.g., subsequent to introduction of DNA encoding the gene product using the method of the invention) include both cell specific and systemic diseases. These diseases can be grouped into several categories including, but not limited to, single gene congenital diseases, multifactorial acquired diseases, tumors, and systemic diseases (e.g., diseases of inadequate or poorly controlled circulating levels of specific polypeptides).

The following examples are put forth so as to provide those of ordinary skill in the art with a complete disclosure and description of how to carry out the invention and are not intended to limit the scope of what the inventors regard as their invention, nor are they intended to represent or imply that the experiments below are all of or the only experiments performed. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, and temperature is in degrees Centigrade.

EXPERIMENTAL

EXAMPLE 1

Synthesis of Cross-linked Cationic Biotinylated Nanoparticles

Methods

Lipids were combined in the following ratio: 39% PC, 30% Gd-chelated lipid, 30% DOTAP, 1% Biotinylated lipid (the Gd cross-linkable monomer was added for in vivo imaging using MRI.)

The combined lipid solutions were evaporated to dryness and dried under high vacuum to remove any residual solvent. The dried lipid film was hydrated to a known lipid density (30 mM) using deionized water. The resulting suspension was then sonicated at temperatures above the gel-liquid crystal phase transition (Tm@64° C.) for 1 hr. using a probe-tip sonicator while maintaining the pH between 7.0 and 7.5 using a 0.1 M sodium hydroxide solution. The resulting nanoparticles were then cross-linked by cooling the solution to 0° C. on a bed of wet ice and irradiating the solution at 254 nm with a hand-held UV lamp for 2 h. The solution was sterile filtered through 0.2 mm filter and stored under argon at room temperature prior to antibody or plasmid conjugation.

An avidin/antibody complex, using the LM609 antibody, which is specific for the integrin $\alpha_v\beta_3$ (see Sipkins et al. (1998) Nat. Med. 4:623-626) was combined with the 30 mM (39% PC/30% Gd-chelated lipid/30% DOTAP/1% Biotinylated lipid) cationic/biotinylated particles in a ratio of 1.4 mg antibody to 1 ml particle and incubated overnight at 4° C. This antibody targeted cationic cross linked nanoparticle was then complexed with a plasmid, as described in Example 3.

EXAMPLE 2

Preparation of Nanoparticles for Ligand Targeted Gene Delivery

Reported here is the synthesis of nanoparticles bearing integrin antagonists that exhibit high avidity to the integrin $\alpha_v\beta_3$ and demonstrate that these materials can be used to deliver nucleic acids to endothelial cells.

Figure 6:
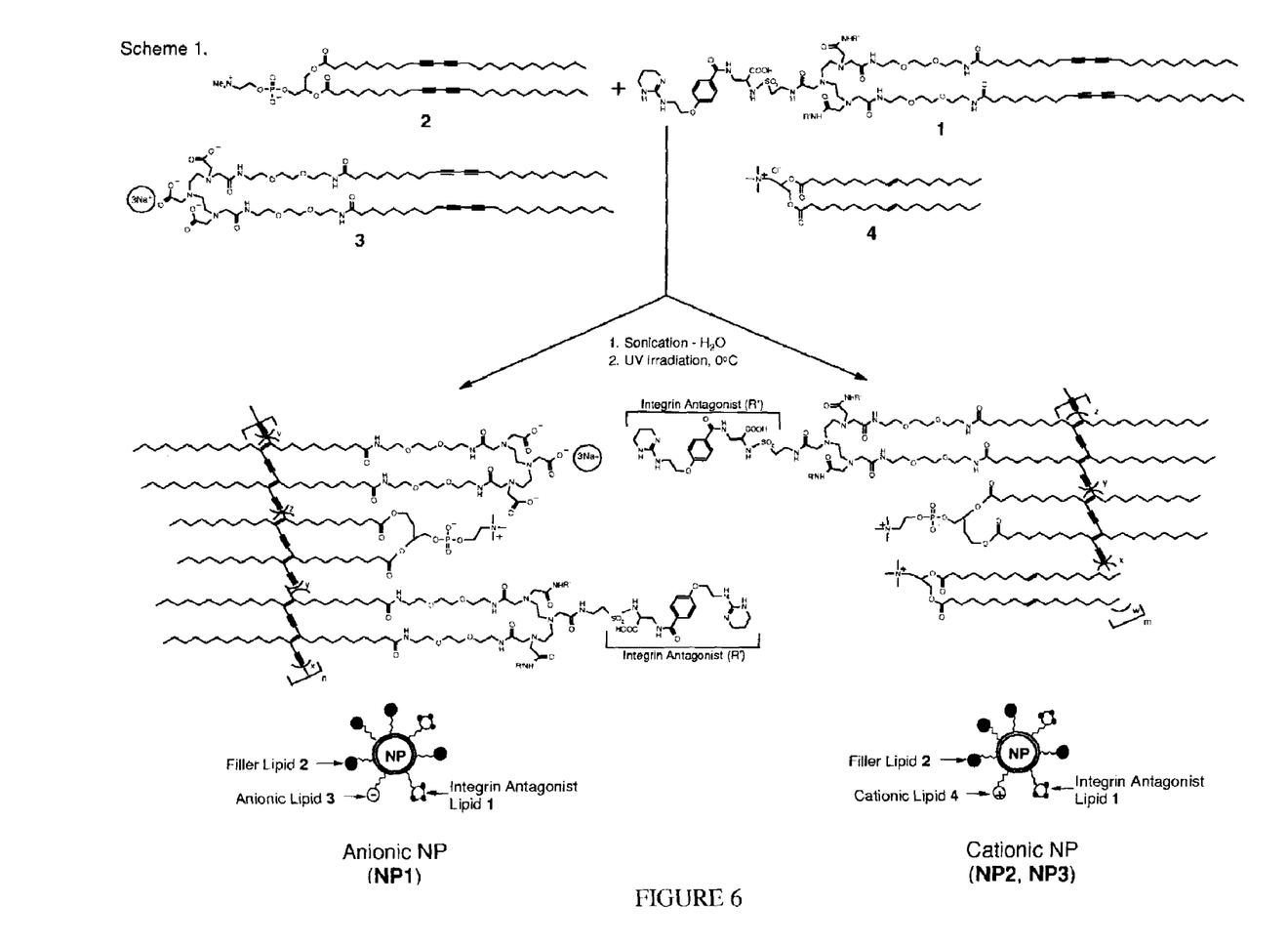
FIG. 6. Scheme 1 outlines the formation of the cross-linked nanoparticles (NPs) by Self-assembly and polymerization of the appropriate amphipathic molecules.

Scheme 1 outlines the formation of the cross-linked nanoparticles (NPs) by self-assembly and polymerization of the appropriate amphipathic molecules. The trivalent lipid-integrin antagonist 1 was combined with commercially available diacetylene phospholipid 2 in a chloroform solution. To this solution was added either the anionic chelator lipid 3 or the cationic lipid 4 in order to control the surface charge. The surface density of the integrin antagonist on the NPs was controlled by varying the concentration of compound 1. To form nanoparticles, the combined lipid solutions were evaporated to dryness and dried under high vacuum to remove any residual solvent. The dried lipid film was hydrated to a known lipid density (30 mM) using deionized water. The resulting suspension was then sonicated at temperatures above the gel-liquid crystal phase transition ($T_m \cong 64°$ C.) for 1 hr. using a probe-tip sonicator while maintaining the pH between 7.0 and 7.5 using a 0.1 M sodium hydroxide solution. The vesicles were then cross-linked by cooling the solution to 0° C. on a bed of wet ice and irradiating the solution at 254 nm with a hand-held UV lamp for 2 h. The resulting NPs (NP1 through NP3) were yellow-orange in color and had two visible absorption bands centered at 490 nm and 535 nm arising from the conjugated eneyne oligomers. The mean diameter of the NPs were between 40 nm and 50 nm as determined by dynamic light scattering and the zeta potential was approximately −50 mV for NP1 and +45 and +37 mV for NP2 and NP3 respectively (Coulter Instruments, Miami, Fla.).

The monomeric lipids 1-4 are used in assembling the cross-linked NPs NP1-NP3. The lipids were combined in the ratios as shown in the accompanying table. These compounds were then sonicated, cooled and cross-linked by irradiation with UV light (254 nm) for 2 hours and then sterile filtered (0.2 µM).

In order to assess the utility of the NPs in targeting the integrins, we constructed cross-linked vesicles with 10 mol % of integrin antagonist lipid complex compound 1 and compounds 2-4 as outlined in Scheme 2. The materials that contained 10 mol % of compound 1 (NP1 and NP3) had the highest avidity for the integrin $\alpha_v\beta_3$. In an in vitro assay for inhibition of cell adhesion using $\alpha_v\beta_3$ positive M21 Melanoma cells binding to vitronectin coated plates, the $IC_{50}$ for the anionic particle NP1 was 0.30 µM equivalents of compound 1 (approximately 2 µM total lipid) on the surface. For the cross-linked nanoparticle NP3, the $IC_{50}$ was 0.40 µM equivalents of compound 1 (approximately 3 µM total lipid). The control particle NP2 showed no inhibition of cell adhesion at similar lipid concentrations (Table 1). Regardless of the surface charge, the targeted NPs have high avidity to the integrins and are able to specifically block the binding of cells expressing the integrin $\alpha_v\beta_3$ in a dose dependant manner.[16]

TABLE 1

| Material | Size (nm) | Zeta Potential (mv) | Cell Adhesion Assay $IC_{50}$ (μM of 1 on NPs) |
|---|---|---|---|
| NP1 | 45.1 ± 0.6 | −42 | 0.30 |
| NP2 | 36.8 ± 0.9 | +45 | No Inhibition |
| NP3 | 41.7 ± 2.2 | +37 | 0.40 |

Physical properties and biological cell adhesion studies on nanoparticles comparing anionic and cationic NPs containing different amounts of the integrin antagonist on the surface. For cell adhesion studies, 64 μM of the free integrin antagonist was required to inhibit 50% of M21 cells binding to vitronectin plate.

Cell adhesion inhibition study was done on plates coated with vitronectin using a human melanoma cell line M21. The multivalent particle complex NP1 and NP3 were separately incubated with M21 cells and applied onto the 48 well plates coated with vitronectin. After 1 h incubation, the wells were washed and the cells that adhered were stained with a solution of crystal violet and the OD at 590 nm was measured. The OD measured was proportional to the number of cells bound to the vitronectin plate and was plotted against the concentration of 1 on the surface of the NPs in different formulations to calculate the $IC_{50}$. The reported values are average of quadruplicate values and have a maximum standard error of ±0.05.

Figure 1:
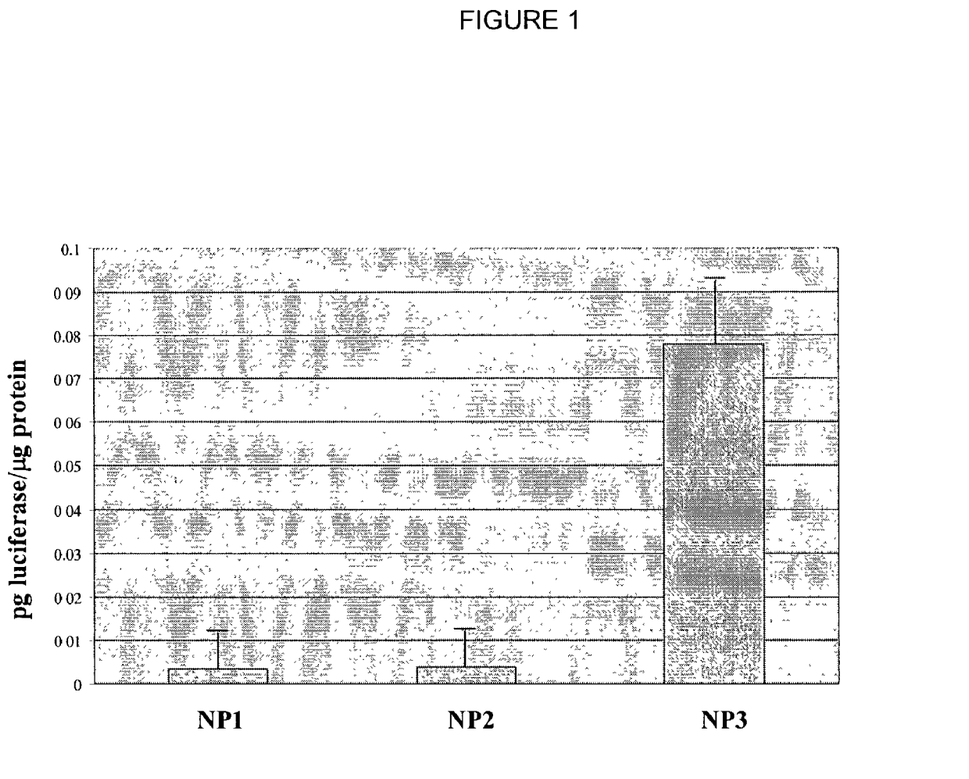
Figure 2:
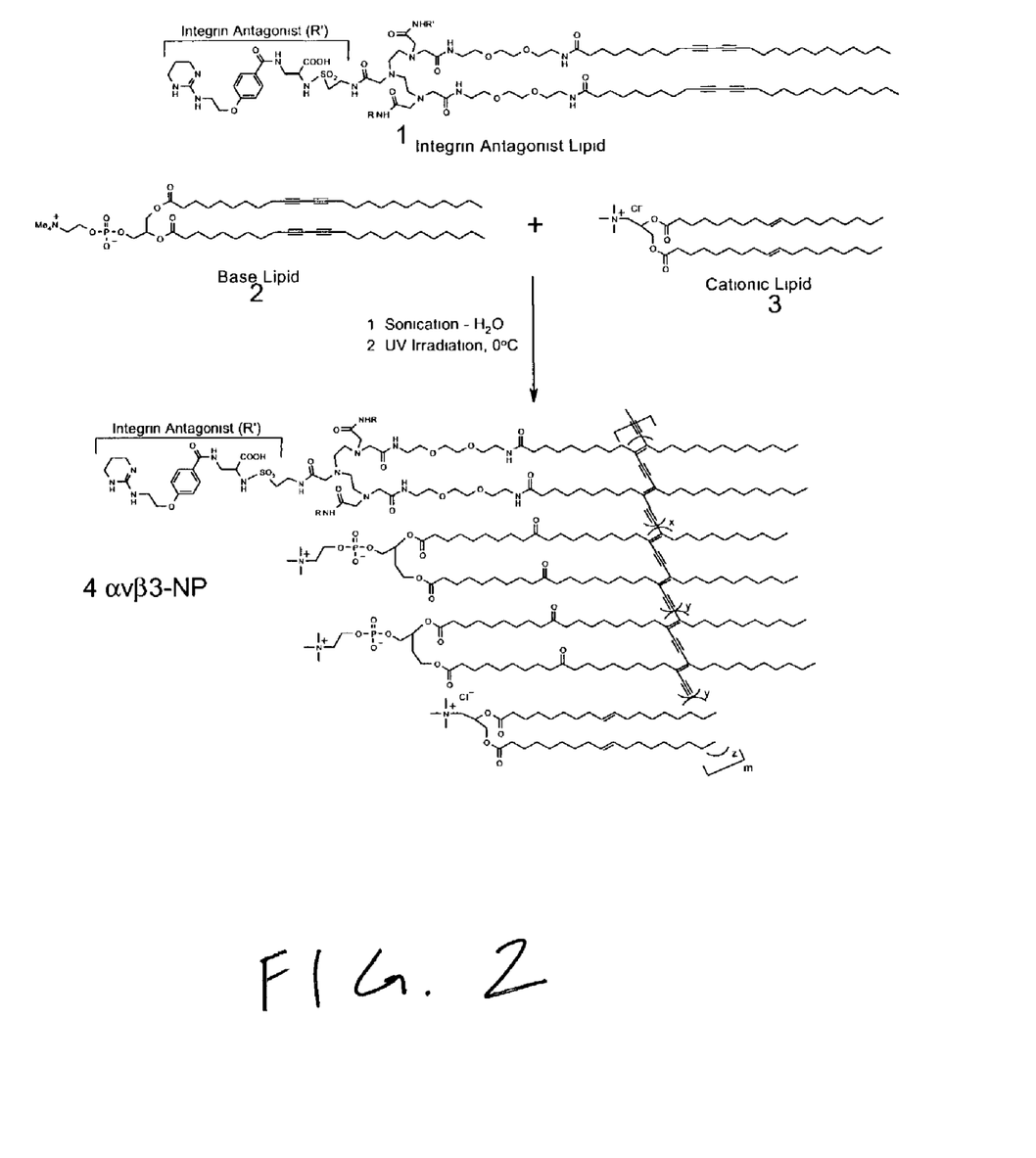
Figure 3A:
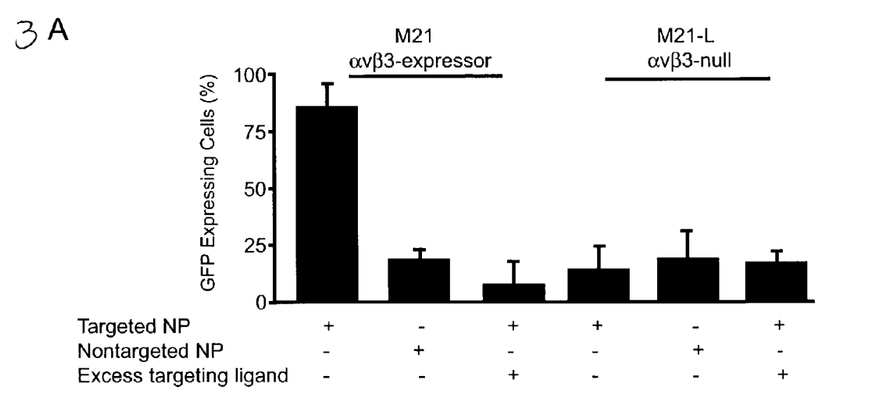
Figure 3B:
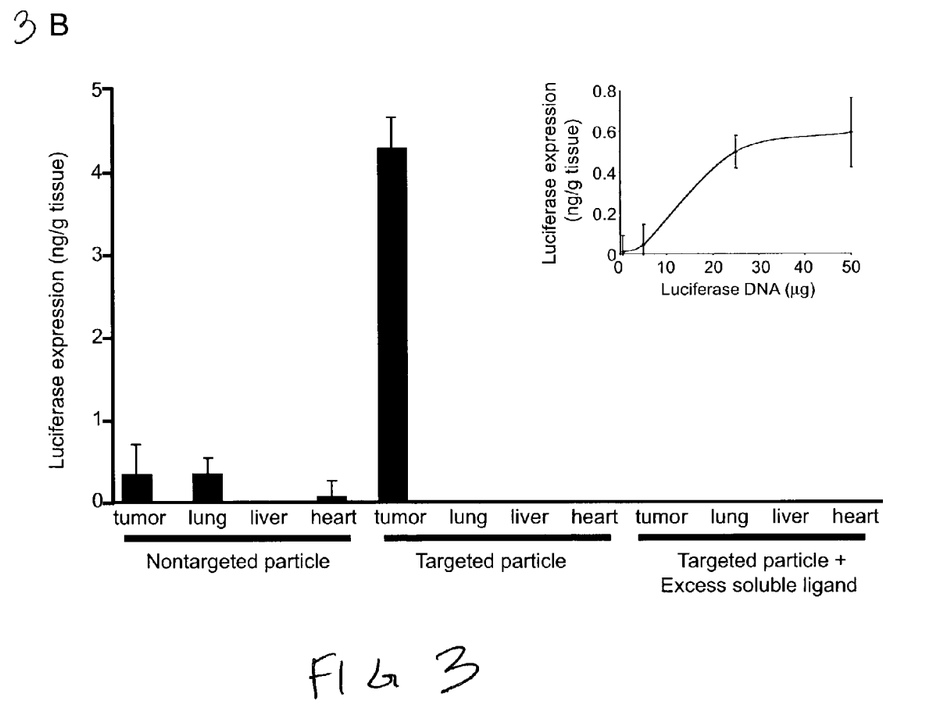

The capability of targeted anionic, non-targeted cationic, and targeted cationic NPs as carriers for gene delivery was tested with endothelial cells in vitro (shown in FIG. 1). Targeted NPs that carry both a cationic and anionic surface contain 10% of 1 (NP1 and NP3) and nontargeted cationic particle NP2 contains 90% of 2 and no 1. To the particle was added plasmid DNA that contained the gene for luciferase (pGL2 luciferase vector from Promega, Madison, Wis.). The plasmid particle complex was formed by incubation of 30 μg of plasmid in 10% dextrose to 15 μL of NPs in distilled water (30 mM) at 27° C. for 1 hr. The complex was then used to treat endothelial cells that express the integrin. The targeted particle (NP3) exhibited a nearly 20 fold increase in transfection efficiency as demonstrated by luciferase expression when compared to non-targeted cationic or targeted anionic NP-plasmid complex (NP2 and NP1 respectively). In subsequent experiments, a 100 fold excess of the free ligand 10 was used to block attachment of the NP-plasmid complex to the cell surface receptors resulting in the same luciferase gene expression profile as the untargeted materials.

Figure 4A:
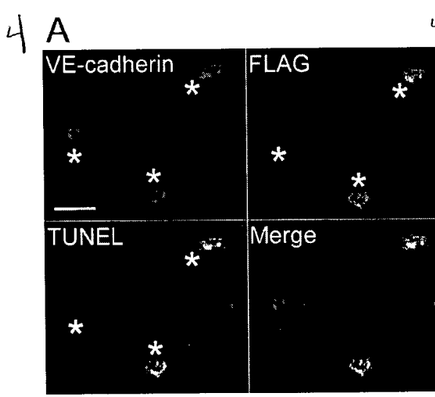
Figure 4B:
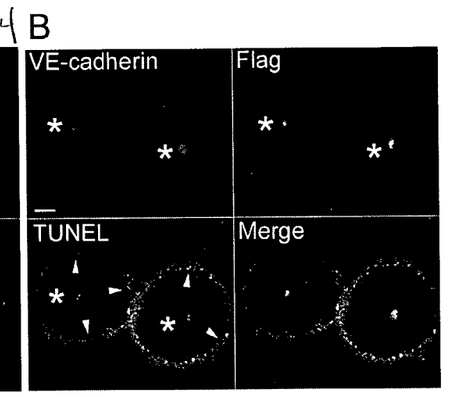
Figure 4C:
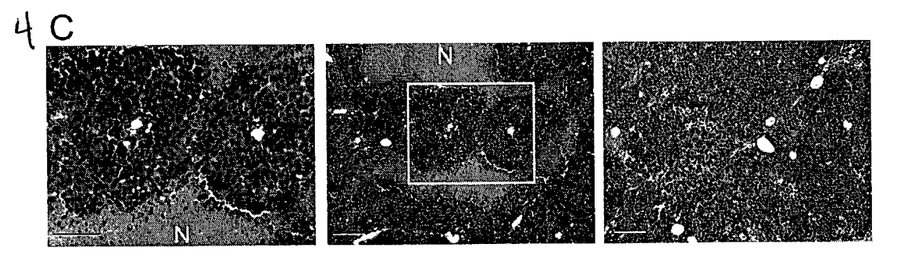

These data demonstrate that ligand arrays of targeting moieties on cross-linked vesicle nanoparticles is a viable method to target vascular surface receptors on endothelial cells. High avidity of the NPs is observed in a cell adhesion assay and these materials have been used to target endothelial cells expressing the integrin $\alpha_v\beta_3$ We have also shown that these materials can specifically deliver genes to endothelial cells and these genes are expressed in vitro.

EXAMPLE 3

In vivo Gene Delivery

During vascular remodeling and angiogenesis, endothelial cells show increased expression of several cell surface molecules that potentiate cell invasion and proliferation. One such molecule is the integrin αvβ3, which plays a key role in endothelial cell survival during angiogenesis in vivo. In addition to its role in cell matrix recognition, αvβ3 may be of particular use in gene delivery strategies since this receptor potentiates the internalization of foot-and-mouth disease virus, rotavirus and adenovirus, thereby facilitating gene transfer. The fact that αvβ3 is preferentially expressed on angiogenic endothelium and contributes to viral internalization prompted its use as an endothelial cell target for non-viral gene delivery.

A cationic cross-linked lipid based NP was synthesized that was covalently coupled to a small organic αvβ3 ligand (αvβ3-NP) (FIG. 2). The αvβ3-binding ligand was selective for αvβ3 in both receptor-binding studies and cell adhesion experiments, with an $IC_{50}$ of 0.04 μM for purified αvβ3 compared to $IC_{50}$ of 5.0 μM for αvβ5 and 2.0 μM for αIIbβ3. In cell adhesion experiments this compound was 100-fold more potent at disrupting αvβ3-mediated than αvβ5-mediated cell attachment to vitronectin (0.30 μM vs. 30 μM, respectively).

To establish that αvβ3-NP could selectively deliver genes to αvβ3 bearing cells, αvβ3-NP was coupled to the gene encoding green fluorescence protein (GFP) and allowed the particles to interact with cultured human melanoma cells expressing αvβ3 (M21) or lacking αvβ3 (M21-L). The αvβ3-NP selectively transduced GFP into M21 cells but not M21-L cells (FIG. 3A). A nontargeted NP (nt-NP), in which the integrin antagonist was replaced by an arginine residue to mimic the zwiterionic surface charge of the αvβ3 targeting ligand, showed no gene delivery to either cell. A 20-fold molar excess of the soluble αvβ3 ligand completely abolished gene delivery to M21 cells, further demonstrating that the selective delivery of the gene is integrin αvβ3-dependent (FIG. 3A).

To determine whether the αvβ3-NP could deliver genes to angiogenic tumor-associated blood vessels, αvβ3-NP or nt-NP complexed with the gene encoding firefly luciferase was injected into the tail vein of mice bearing αvβ3 negative M21-L melanomas. After 24 hours, maximal luciferase activity was detected in tumors after injection of NP coupled to 25 μg luciferase (FIG. 3B- inset). At this dose, minimal luciferase was detected in the lung and heart (FIG. 3B) and no detectable expression was found in the liver, brain, kidney, skeletal muscle, spleen, and bladder. Tumor-specific luciferase expression was completely blocked when mice were co-injected with a 20-fold molar excess of the soluble αvβ3-targeting ligand (FIG. 3B).

Components of the Ras-Raf-MEK-ERK pathway appear to play a significant role in neovascularization since blockade of this pathway suppresses angiogenesis in vivo. We focused on a mutant form of Raf-1 that fails to bind ATP ($ATP^{\mu}$-Raf) and that blocks endothelial cell Raf activity in cultured endothelial cells. This mutant also blocks angiogenesis on the chick chorioallantoic membrane in response to basic fibroblast growth factor (bFGF) or vascular endothelial cell growth factor (VEGF). In fact, mice lacking Raf-1 die early in development with high levels of cellular apoptosis and vascular defects in the yolk sac and placenta.

To validate the vascular targeting capacity of this particle and to establish a role for Raf-1 in angiogenesis, a cDNA encoding FLAG-tagged $ATP^{\mu}$-Raf was coupled to the αvβ3-NP (αvβ3-NP/Raf(−)). M21-L melanomas implanted subcutaneously were allowed to grow for 9 days at which time they reached a size of ~400 $mm^3$. We injected tumor-bearing mice intravenously (i.v.) with the αvβ3-NP/Raf(−). After 24 or 72 hours we removed the tumors and co-stained them with anti-VE-cadherin antibody to identify blood vessels and anti-FLAG to detect gene expression. The tumors were also evaluated for TUNEL staining to mark apoptotic cells, since suppression of Raf activity has been reported to promote apoptosis. Twenty-four hours after injection of αvβ3-NP/Raf (−) TUNEL positive cells were only detected among the vessels that had been transduced (FLAG) (FIG. 4A). To assess the impact of ATP$^\mu$-Raf on tumor cell viability, we stained cryosections taken from tumors 72 hours after treatment and examined them at lower magnification (100×) to evaluate both blood vessels and surrounding tumor parenchyma. In addition to the apoptosis among the blood vessels (VE-Cadherin positive), there were concentric rings of apoptosis (TUNEL) among the tumor cells proximal to each apoptotic vessel (FIG. 4B). Accordingly, hematoxylin and eosin revealed extensive tumor necrosis (FIG. 4C).

Figure 5A:
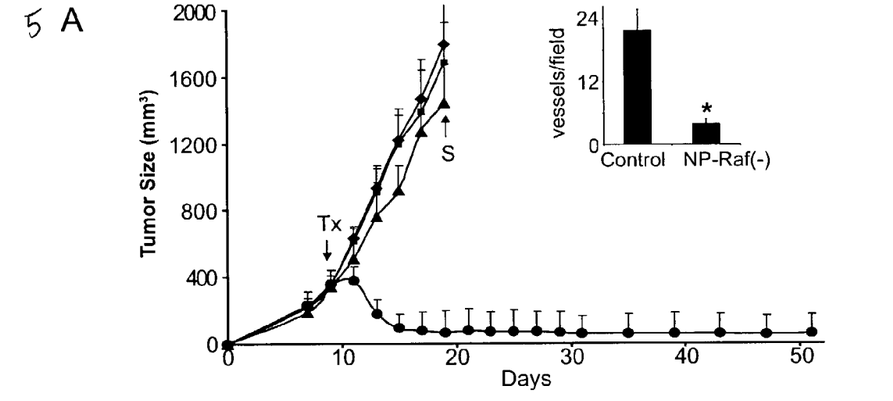
Figure 5B:
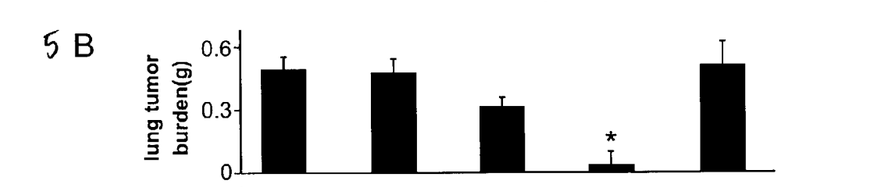
Figure 5C:
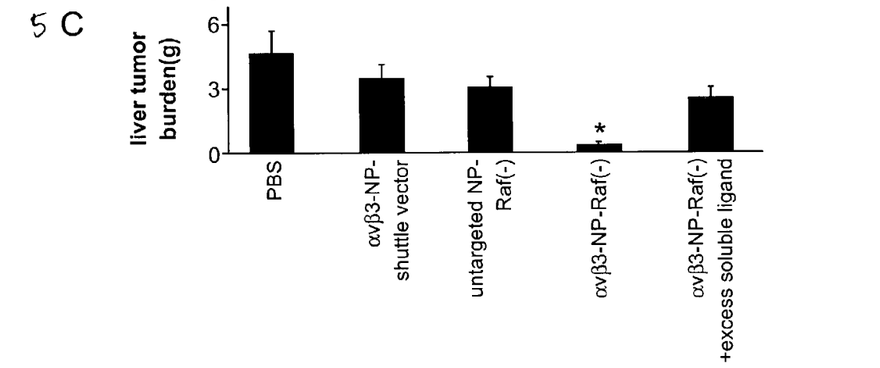

To further test the therapeutic efficacy of this construct, we randomized mice bearing established 400 mm$^3$ M21-L tumors into four groups and treated them with a single tail vein injection of (control), nt-NP/Raf(−), or $\alpha v\beta 3$-NP/Raf (−). The fourth group was co-injected with $\alpha v\beta 3$-NP/Raf(−) plus a 20-fold molar excess of the soluble $\alpha v\beta 3$-targeting ligand. Mice injected with PBS or nt-N P/Raf(−) formed large tumors (1200 mm$^3$) and consequently were euthanized on day 25 (FIG. 5A). In contrast, mice injected with $\alpha v\beta 3$-NP/Raf(−) displayed rapid tumor regression (FIG. 5A). Six days after treatment, 4 of 6 mice showed no evidence of tumor and the two others showed a >95% reduction in tumor mass and >75% suppression of blood vessel density (FIG. 5C). Importantly, these tumor regressions were sustained for >250 days. Injection of excess soluble $\alpha v\beta 3$ ligand, while slightly suppressing tumor growth on its own, completely abolished the anti-tumor activity of $\alpha v\beta 3$-NP/Raf(−) (FIG. 5A). These findings demonstrate that $\alpha v\beta 3$-targeted delivery of ATP$^\mu$-Raf to blood vessels causes tumor regression based on its ability to promote apoptosis of the angiogenic endothelium. The fact that M21-L tumors lack $\alpha v\beta 3$, and are not transduced by $\alpha v\beta 3$-NP, suggests that the anti-tumor effect is based on the anti-angiogenic effects and not a direct effect on the tumor.

Figure 5D:
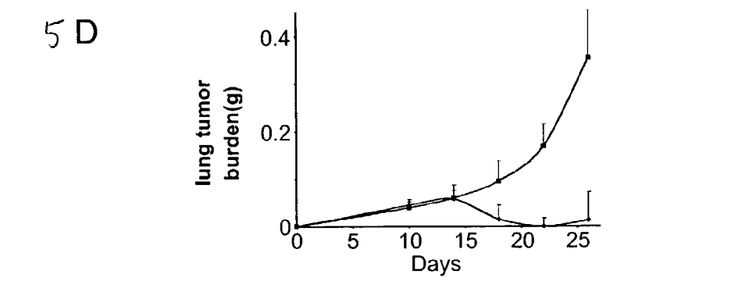

We next examined whether this therapy was effective against established syngeneic pulmonary and hepatic metastases of colon carcinoma. To this end, murine CT-26 carcinoma cells were either injected intravenously or intrasplenically into Balb/C mice. This procedure typically results in the formation of experimental lung or liver metastases, respectively, within four days. However, in our study, the pulmonary or hepatic metastases were established for 10 days prior to treatment with the NP/gene complexes to ensure that all animals contained actively growing lung or liver tumors. Control mice treated with PBS, $\alpha v\beta 3$-NP complexed to a control vector, or a nt-NP/Raf(−) showed extensive tumor burden in the lungs or livers of these animals (FIGS. 5B and C). In contrast, mice treated with $\alpha v\beta 3$-NP/Raf(−) displayed little or no visible tumor metastases (FIGS. 5B and C) as demonstrated by a significant reduction in wet lung or liver weight (FIGS. 5C and D). Mice injected with $\alpha v\beta 3$-NP/Raf(−) along with a 20-fold molar excess of soluble targeting ligand had a tumor burden similar to that in control mice, demonstrating that this response is $\alpha v\beta 3$-specific (FIGS. 5B and C). In a parallel study in which mice were euthanized and tumor volume established during the course of the experiment, $\alpha v\beta 3$-NP-Raf(−) was shown to cause regression of pulmonary metastases (FIG. 5D).

In summary these data demonstrate that pronounced tumor regressions can be achieved by systemic delivery of a ligand targeted cross-linked nanoparticle complexed with a therapeutic gene to impart an anti-angiogenic effect that is targeted to the tumor vasculature. Several components of this strategy likely contribute to its pronounced anti-tumor activity and these may be useful for similar treatments in humans. First, the NP used in this study has multivalent targeting of integrin $\alpha v\beta 3$ that selectively delivers genes to angiogenic blood vessels. A similar particle containing gadolinium and the anti-$\alpha v\beta 3$ targeting antibody, LM609, has been successfully used to image angiogenic blood vessels in tumor-bearing rabbits. Second, the mutant Raf-1 gene delivered to these tissues influences the signaling cascades of two prominent angiogenic growth factors, bFGF and VEGF. The robust pro-apoptotic activity of this gene is consistent with previous studies revealing a role for Raf-1 in promoting cell survival. Finally, because nanoparticles are less immunogenic than viral vectors, it may be feasible to deliver therapeutic genes repeatedly to angiogenic blood vessels for sustained treatment of diseases that depend on angiogenesis and vascular remodeling.

Materials and Methods

| | | Physical Characteristics of $\alpha v\beta 3$-NP | | |
|---|---|---|---|---|
| Material | Size (nm) | Zeta Potential (mv) | Cell Adhesion Assay IC$_{50}$ ($\mu$M of $\alpha v\beta 3$ ligand on NPs)$^\S$ | Effect of Multivalency IC$_{50}$ (Free [$\alpha v\beta 3$ ligand]/[[$\alpha v\beta 3$ ligand] on NPs)$^{\S\S}$ |
| $\alpha v\beta 3$-NP | 41.7 ± 2.2 | +35 | 0.40 | 183 |

Cell adhesion inhibition study was done on plates coated with vitronectin using a human melanoma cell line M21. The multivalent particle complex $\alpha v\beta 3$-NP as well as the monomeric $\alpha v\beta 3$ ligand were separately incubated with M21 cells and applied onto the 48 well plates coated with vitronectin. After 1 h incubation, the wells were washed and the cells that adhered were stained with a solution of crystal violet and the OD at 590 nm was measured. The OD measured was proportional to the number of cells bound to the vitronectin plate and was plotted against the concentration of 10 on the surface of the NPs in different formulations to calculate the IC$_{50}$. The reported values are average of quadruplicate values and have a maximum standard error of ±0.05. The multivalency effect was calculated by dividing the IC$_{50}$ for free $\alpha v\beta 3$ ligand by the IC$_{50}$ of the concentration of $\alpha v\beta 3$-NP.

Generation of $\alpha v\beta 3$-NP-DNA Particles. DNA and $\alpha v\beta 3$-NP were mixed in a ratio of 25 $\mu$gs of CsCl purified DNA:450 nanomoles of $\alpha v\beta 3$-NP/200 $\mu$l injection volume. Prior to mixing all solutions were warmed to 37° C. For each mouse injected, 15 $\mu$l of 30 mM $\alpha v\beta 3$-NP and 25 $\mu$g of DNA were diluted into seperate 100 $\mu$l volumes of 5% dextrose (pH 7.2). The DNA mixture was then rapidly pipetted into the $\alpha v\beta 3$-NP solution. Precipitation as observed visually or by light scattering was not detected in any solutions in which the DNA had been CsCl purified. DNA-$\alpha v\beta 3$-NP was generally injected into the treatment mice within 48 hours of preparation.

Immunostaining. At time of tumor resection, animals were first anesthetized followed by animal followed by opening the right atria and intracardial perfusion with 1 ml of heparinized saline. Tumors are then resected and fixed in Zn-formalin buffer followed by paraffin embedding and sectioning.

To further reduce autofluorescence, slides were incubated 3× for 10 minutes following paraffin removal in a fresh ice-cold 1 mg/ml solution of sodium borohydride solution in PBS on ice immediately before use. Slides were further pretreated using a microwave citrate protocol. Slides were then rinsed in PBS and treated for TUNEL staining according to manufacturer's directions (Apoptag kit, Serologicals, Inc., GA.) with the exception that primary antibodies directed against FLAG (Zymed, OR) and VE-Cadherin (Santa Cruz Biotechnologies, CA) were applied in conjunction with the anti-digoxigenin for TUNEL followed by blocking in normal goat serum, and exposure to secondary antibodies conjugated to Alexa fluors (Molecular Probes, OR). Slides were then mounted and visualized using confocal microscopy.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition for in vivo gene delivery, comprising:
    a complex of nucleic acid and targeting cross-linked nanoparticles,
    wherein said targeting cross-linked nanoparticle comprises:
    cross-linked neutral amphipathic molecules (NAM) comprising a hydrophilic head group; a hydrophobic tail group; and a linker or covalent bond between the head and tail groups, and further comprising a crosslinking functional group providing for oligomer formation,
    cationic amphipathic molecules (CAM) comprising a hydrophilic head group; a hydrophobic tail group; and a linker or covalent bond between the head and tail groups, and is positively charged; and
    targeting amphipathic molecules (TAM) comprising a hydrophilic head group; a hydrophobic tail group; and a linker or covalent bond between the head and tail groups, and further comprising a covalently bound targeting moiety other than a non-peptidic $a_vb_3$ integrin antagonist,
    in the proportions wherein said CAM comprise from about 5 to 40% by weight of the total amphipathic molecules, and said TAM comprises from about 1 to 20% by weight of the total amphipathic molecules; wherein each of said amphipathic molecules are lipid molecules, and wherein said complex is formed by crosslinking of said nanoparticles and following formation of said nanoparticles, mixing said nanoparticles with said nucleic acid.

2. The composition according to claim 1, wherein said NAM are cross-linked oligomers of from 2 to 100 monomers.

3. The composition according to claim 2, wherein said targeting cross-linked nanoparticle has a zeta potential of from +5 mV to not more than +75 mV.

4. The composition according to claim 3, wherein said complex of nucleic acid and targeting cross-linked nanoparticle is from 50 nm to 400 nm in diameter.

5. The composition according to claim 4, wherein said nucleic acid is DNA.

6. The composition according to claim 5, wherein said nucleic acid is closed, circular, double stranded DNA.

7. The composition according to claim 4, further comprising a physiologically acceptable, low salt medium.

8. A method of in vivo delivery of a nucleic acid to a targeted site, the method comprising:
    administering to an animal a composition according to claim 1.

9. The method according to claim 8, wherein said NAM are cross-linked oligomers of from 2 to 100 monomers.

10. The method according to claim 9, wherein said targeting cross-linked nanoparticle has a zeta potential of from +5 mV to not more than +75 mV.

11. The method according to claim 10, wherein said complex of nucleic acid and targeting cross-linked nanoparticle is from 50 nm to 400 nm in diameter.

12. The method according to claim 11, wherein said nucleic acid is DNA.

13. The method according to claim 12, wherein said nucleic acid is closed, circular, double stranded DNA.

14. The method according to claim 8, wherein said complex of nucleic acid and targeting cross-linked nanoparticle further comprises a physiologically acceptable, low salt medium.

* * * * *